United States Patent [19]

Rohde

[11] Plant 4,125

[45] Oct. 11, 1977

[54] BEGONIA PLANT

[75] Inventor: Hans Joachim Rohde, Nurtingen, Germany

[73] Assignee: Mikkelsens Inc., Ashtabula, Ohio

[21] Appl. No.: 715,102

[22] Filed: Aug. 17, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Donald D. Jeffery

[57] ABSTRACT

This novel begonia was discovered as a mutation of Nixe, and principally differs therefrom by its appleblossom pink tepals.

1 Drawing Figure

The present invention relates to a new and distinctive cultivar of begonia plant, botanically known as *Begonia elatior,* (hiemalis-Fotsch) and known by the cultivar name Elfe. The new cultivar is a mutation of the cultivar Nixe and was discovered in a group of flowering plants of the parent cultivar. The cultivar Nixe is disclosed in the pending applicaton of Margarette Rohde-Rieger, Ser. No. 596,453, filed July 16, 1975. Asexual reproduction of the new cultivar by stem and leaf cuttings has reproduced the unique features of the cultivar through successive propagations.

The following characteristics in combination distinguish the new begonia from both its parent and other begonias commercially known and used in the floriculture industry:

1. Bright appleblossom pink double flowers, compared to the red flowers of the parent variety Nixe. Elfe has somewhat fewer petals than parent.
2. Short, full, compact, and upright growth.
3. A very high degree of self-branching, thereby resulting in the new cultivar being valuable for commercial pot plant production and for propagation by stem cuttings.
4. Round, heavily textured dark green foliage with nearly complete edges.
5. Leaf cuttings propagate 7 to 14 days more rapidly than the variety Schwabenland, disclosed in U.S. Plant Pat. No. 3,320, granted to Otto Rieger Mar. 13, 1973.
6. Leaf cuttings consistently produce four to six adventitious shoots at all times of the year whereas the well known Schwabenland types are inconsistent in the summer months.
7. Keeping quality of the flowers is better than in the Schwabenland types, but more importantly the flowering persists for 4 to 6 weeks longer.
8. Leaf area is very uniform on each plant and remains quite constant at maturity. Plant spacing can be decreased without jeopardizing quality.
9. Plant growth stays short and compact in all seasons so that growth retardants are not needed in summer months.

The accompanying colored photograph illustrates the overall appearance of the new cultivar when grown under commercial practices in Nurtingen, Germany, and shows the colors as true as it is reasonably possible to obtain in a colored reproduction of this type.

The following is a detailed description of my new begonia variety based on plants produced under commercial practices in Nurtingen, Germany. Color references are made to the Royal Horticultural Society Colour Chart except where general color terms of ordinary dictionary significance are used.

Parentage: The new cultivar is a mutation of the cultivar Nixe.

Propagation: Leaf cuttings produce a saleable young plant with consistently four or more shoots in 7–14 less days than the cultivar Schwabenland, disclosed in U.S. Plant Pat. No. 3,320. Profuse self branching also allows the new cultivar to be propagated by stem cuttings in 4 weeks.

Rooting habit: Either leaf cuttings or stem cutting will develop fine dentritic roots in 4 weeks. However, the roots are fine and sensitive and not particularly strong. Loose and mild soil is therefore necessary.

Plant form: Upright and compact.

Habit of growth: Medium rate of growth for this class of begonia, producing an upright, self branching, close internoded, compact plant.

Blooming habit: Very profuse flowering over an extended period of time.

Blooming season: Natural blooming season is in November but with controlled environmental conditions of temperature and daylight this variety can be brought into flower anytime of the year.

Foliage: Quite dense, roundish and uniform in size and shape at maturity.

*Size.*—Approximately 10 cm. across by 8 cm. long.

*Shape.*—Nearly circular with very little sinus indentation.

*Texture.*—Leathery.

*Margin.*—Very fine serration.

*Color.*—Young, top — yellow green 147A. Young, underside — red-purple 60A. Mature, top — darker than 139A. Mature, underside — green, heavily infused with red-purple 60A.

Disease resistance: Resistance to powdery mildew is about the same as in the parent cultivar and the above noted Schwagenland cultivar when plants are grown under conditions favorable to that disease.

FLOWERS

Borne: On strong upright peduncles with two or three originating at the same point on the main flowering stem. This feature tends to give the appearance of several flowers clustered together in the floral display.

Quantity: Flowers in bloom at one time is somewhat above average for elatior type begonias.

Flower Buds: Flat, measuring approximately 2 cm. in diameter before opening.

Tepals: Semi-double type, numbering between 12 to 15, measuring 25 mm. wide by 30 mm. long. Total flower size is 5 to 6 cm. in diameter.

*Tepal color.*—Topside red 49A-B. The color of the underside of the first two tepals is red 41-B, and the color of the underside of the other tepals is red 48-C.

Reproductive organs:

*Stamens.*—None seen to date.

*Pollen.*—None seen to date.

*Styles/ovaries.*—None seen to date.

I claim:

1. A new and distinct cultivar of begonia plant characterized particularly by the combined characteristics of bright, appleblossom pink colored, double flowers; short full compact and upright growth habit in all seasons; a high degree of self-branching; round, heavily textured dark green foliage with nearly complete edges; rapid propagation from leaf cuttings, with the cuttings consistently producing four to six adventitious shoots at all times of the year; excellent keeping quality and long flowering period, and by the uniform leaf area on each plant.

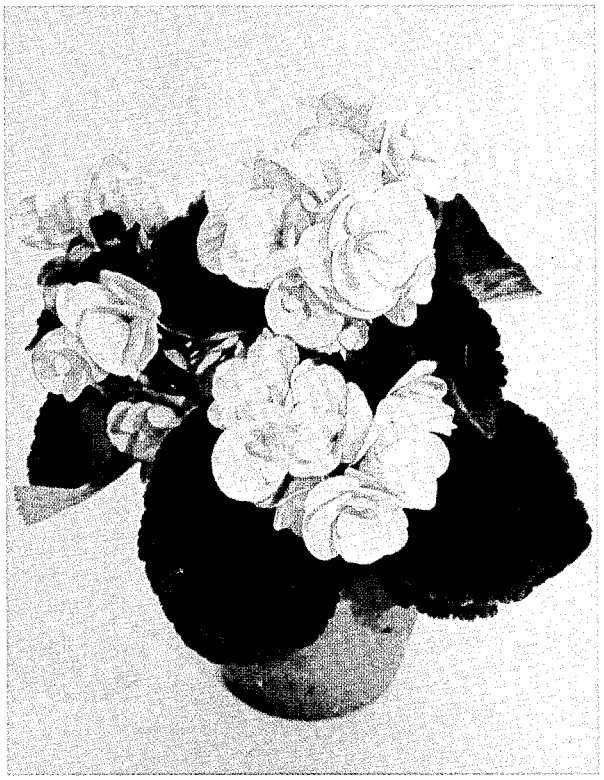

* * * * *